US008615116B2

(12) United States Patent
Lardo et al.

(10) Patent No.: US 8,615,116 B2
(45) Date of Patent: Dec. 24, 2013

(54) COMBINED MULTI-DETECTOR CT ANGIOGRAPHY AND CT MYOCARDIAL PERFUSION IMAGING FOR THE DIAGNOSIS OF CORONARY ARTERY DISEASE

(75) Inventors: Albert Clark Lardo, Baldwin, MD (US); Richard T. George, Monkton, MD (US); Joao A. C. Lima, Baltimore, MD (US); Eduardo T. Marban, Beverly Hills, CA (US); Takashi Ichihara, Nagoya (JP)

(73) Assignees: The Johns Hopkins University, Baltimore, MD (US); Toshiba Medical Systems Corporation, Otawara-shi, Tochigi-ken (JP)

( * ) Notice: Subject to any disclaimer, the term of this patent is extended or adjusted under 35 U.S.C. 154(b) by 0 days.

(21) Appl. No.: 12/680,152

(22) PCT Filed: Sep. 29, 2008

(86) PCT No.: PCT/US2008/011265
§ 371 (c)(1),
(2), (4) Date: Aug. 5, 2010

(87) PCT Pub. No.: WO2009/045368
PCT Pub. Date: Apr. 9, 2009

(65) Prior Publication Data
US 2011/0110488 A1 May 12, 2011

Related U.S. Application Data

(60) Provisional application No. 60/995,857, filed on Sep. 28, 2007.

(51) Int. Cl.
G06K 9/00 (2006.01)
A61B 6/00 (2006.01)

(52) U.S. Cl.
USPC .............. 382/128; 382/130; 382/131; 378/4; 378/8

(58) Field of Classification Search
USPC .......................................... 378/4, 8
See application file for complete search history.

(56) References Cited

U.S. PATENT DOCUMENTS 5,960,054 A * 9/1999 Freeman et al. .................. 378/4
6,337,992 B1 * 1/2002 Gelman ........................ 600/425
(Continued)

OTHER PUBLICATIONS

International Search Report PCT/US08/11265.
(Continued)

*Primary Examiner* — Alexander H Taningco
(74) *Attorney, Agent, or Firm* — Venable LLP; Henry J. Daley

(57) ABSTRACT

A computed tomography system has a support stage constructed and arranged to support a subject while under observation, an x-ray illumination system arranged proximate the support stage to illuminate the subject with x-rays, an x-ray detection system arranged proximate the support stage to detect x-rays after they pass through the subject and to provide signals based on the detected x-rays, and a data processing system in communication with the x-ray detection system to receive the signals from the x-ray detection system. The computed tomography system has a dynamic mode of operation and a scanning mode of operation. The data processing system extracts information concerning a dynamic process of the subject based on signals from both the dynamic mode and the scanning mode of operation.

21 Claims, 9 Drawing Sheets

(56) References Cited

U.S. PATENT DOCUMENTS

| | | | | |
|---|---|---|---|---|
| 6,442,235 | B2* | 8/2002 | Koppe et al. | 378/62 |
| 6,628,743 | B1* | 9/2003 | Drummond et al. | 378/8 |
| 6,782,071 | B1* | 8/2004 | Tsuyuki | 378/4 |
| 7,020,511 | B2 | 3/2006 | Boyd | |
| 7,251,308 | B2 | 7/2007 | Tsuyuki | |
| 7,450,743 | B2* | 11/2008 | Sundar et al. | 382/128 |
| 7,725,165 | B2* | 5/2010 | Chen et al. | 600/425 |
| 7,756,317 | B2* | 7/2010 | Huo et al. | 382/132 |
| 7,912,270 | B2* | 3/2011 | Skinner et al. | 382/131 |
| 2002/0181645 | A1* | 12/2002 | Bruder et al. | 378/8 |
| 2003/0128801 | A1* | 7/2003 | Eisenberg et al. | 378/19 |
| 2003/0161435 | A1* | 8/2003 | Ozaki | 378/4 |
| 2003/0161436 | A1* | 8/2003 | Boyd et al. | 378/8 |
| 2004/0008819 | A1* | 1/2004 | Drummond et al. | 378/162 |
| 2004/0052409 | A1* | 3/2004 | Bansal et al. | 382/128 |
| 2006/0018424 | A1* | 1/2006 | Bruder et al. | 378/15 |
| 2006/0050840 | A1* | 3/2006 | Ikeda et al. | 378/8 |
| 2006/0241402 | A1 | 10/2006 | Ichihara et al. | |
| 2009/0129536 | A1* | 5/2009 | Ichihara et al. | 378/4 |

OTHER PUBLICATIONS

Raff GL, Gallagher MJ, O'Neill WW, et al. Diagnostic accuracy of noninvasive coronary angiography using 64-slice spiral computed tomography. *J Am Coll Cardiol.* Aug. 2, 2005;46(3):; pp. 552-557.

Leschka S, Alkadhi H, Plass A, et al. Accuracy of MSCT coronary angiography with 64-slice technology: first experience. *Eur Heart J.* Aug. 2005; 26(15): pp. 1482-1487.

Leber AW, Knez A, von Ziegler F, et al. Quantification of obstructive and nonobstructive coronary lesions by 64-slice computed tomography: a comparative study with quantitative coronary angiography and intravascular ultrasound. *J Am Coll Cardiol.* Jul. 5, 2005;46(1): pp. 147-154.

Mollet NR, Cademartiri F, Nieman K, et al. Multislice spiral computed tomography coronary angiography in patients with stable angina pectoris. *J Am Coll Cardiol.* Jun. 16, 2004;43(12): pp. 2265-2270.

Hacker M, Jakobs T, Matthiesen F, et al. Comparison of spiral multidetector CT angiography and myocardial perfusion imaging in the noninvasive detection of functionally relevant coronary artery lesions: first clinical experiences. *J Nucl Med.* Aug. 2005;46(8): pp. 294-1300.

Rispler S, Keidar Z, Ghersin E, et al. Integrated single-photon emission computed tomography and computed tomography coronary angiography for the assessment of hemodynamically significant coronary artery lesions. *J Am Coll Cardiol.* Mar. 13, 2007;49(10): pp. 1059-1067.

Schuijf JD, Wijns W, Jukema JW, et al. Relationship between noninvasive coronary angiography with multi-slice computed tomography and myocardial perfusion imaging. *J Am Coll Cardiol.* Dec. 19, 2006;48(12): pp. 2508-2514.

Christian TF, Rettmann DW, Aletras AH, et al. Absolute myocardial perfusion in canines measured by using dual-bolus first-pass MR imaging. *Radiology.* Sep. 2004;232(3): pp. 677-684.

Jerosch-Herold M, Wilke N, Stillman AE. Magnetic resonance quantification of the myocardial perfusion reserve with a Fermi function model for constrained deconvolution. *Med Phys.* Jan. 1998;25(1):73-84.

Schelbert HR, Phelps ME, Huang SC, et al. N-13 ammonia as an indicator of myocardial blood flow. *Circulation.* Jun. 1981;63(6): pp. 1259-1272.

Mohlenkamp S, Behrenbeck TR, Lerman A, et al. Coronary microvascular functional reserve: quantification of long-term changes with electron-beam CT preliminary results in a porcine model. *Radiology.* Oct. 2001;221(1): pp. 229-236.

Rumberger JA, Feiring AJ, Lipton MJ, et al. Use of ultrafast computed tomography to quantitate regional myocardial perfusion: a preliminary report. *J Am Coll Cardiol.* Jan. 1987;9(1): pp. 59-69.

Wang T WX, Chung N, et al. Myocardial Blood Flow Estimated by Synchronous Multislice, High-Speed Computed Tomography. *IEEE Trans. Med. Imaging.* 1989 1989; pp. 8:70-77.

Wolfkiel CJ, Ferguson JL, Chomka EV, et al. Measurement of myocardial blood flow by ultrafast computed tomography. *Circulation.* Dec. 1987;76(6): pp. 1262-1273.

Wu XS, Ewert DL, Liu YH, et al. In vivo relation of intramyocardial blood volume to myocardial perfusion. Evidence supporting microvascular site for autoregulation. *Circulation.* Feb. 1992;85(2): pp. 730-737.

Reinhardt CP, Dalhberg S, Tries MA, et al. Stable labeled microspheres to measure perfusion: validation of a neutron activation assay technique. *Am J Physiol Heart Circ Physiol.* Jan. 2001;280(1): pp. H108-H116.

Cerqueria, et al. Standardized myocardial segmentation and nomenclature for tomographic imaging of the heart: a statement for healthcare professionals from the Cardiac Imaging Committee of the Council on Clinical Cardiology of the American Heart Association. *Circulation.* Jan. 29, 2002;105(4): pp. 539-542.

George RT, Silva C, Cordeiro MA, et al. Multidetector computed tomography myocardial perfusion imaging during adenosine stress. *J Am Coll Cardiol.* Jul. 4, 2006;48(1): pp. 153-160.

Williams RL. A note on robust variance estimation for cluster-correlated data. *Biometrics.* Jun. 2000;56(2): pp. 645-646.

Canty JM, Jr., Judd RM, Brody AS, et al. First-pass entry of nonionic contrast agent into the myocardial extravascular space. Effects on radiographic estimates of transit time and blood volume. *Circulation.* Nov. 1991;84(5): pp. 2071-2078.

Tong CY, Prato FS, Wisenberg G, et al. Measurement of the extraction efficiency and distribution volume for Gd-DTPA in normal and diseased canine myocardium. *Magn Reson Med.* Sep. 1993;30(3): pp. 337-346.

Tweedle MF. Physicochemical properties of gadoteridol and other magnetic resonance contrast agents. *Invest Radiol.* Aug. 1992;27 Suppl 1:S2-6.

\* cited by examiner

COMBINED MULTI-DETECTOR CT ANGIOGRAPHY AND CT MYOCARDIAL PERFUSION IMAGING FOR THE DIAGNOSIS OF CORONARY ARTERY DISEASE

CROSS-REFERENCE TO RELATED APPLICATION

This application claims priority to U.S. Provisional Application No. 60/995,857 filed Sep. 28, 2007, the entire contents of which are hereby incorporated by reference, and is a U.S. national stage application under 35 U.S.C. §371 of PCT/US2008/011265 filed Sep. 29, 2008, the entire contents of which are incorporated herein by reference.

BACKGROUND

1. Field of Invention

This application relates to computed tomography systems and more particularly to multi-detector computed tomography systems for combined myocardial perfusion imaging and the diagnosis of coronary artery disease.

2. Discussion of Related Art

The contents of all references, including articles, published patent applications and patents referred to anywhere in this specification are hereby incorporated by reference.

Multidetector computed tomography coronary angiography (MDCTA) provides non-invasive assessment of coronary atherosclerosis (Raff G L, Gallagher M J, O'Neill W W, et al. Diagnostic accuracy of noninvasive coronary angiography using 64-slice spiral computed tomography. *J Am Coll Cardiol*. Aug. 2 2005; 46(3):552-557; Leschka S, Alkadhi H, Plass A, et al. Accuracy of MSCT coronary angiography with 64-slice technology: first experience. *Eur Heart J*. August 2005; 26(15):1482-1487; Leber A W, Knez A, von Ziegler F, et al. Quantification of obstructive and nonobstructive coronary lesions by 64-slice computed tomography: a comparative study with quantitative coronary angiography and intravascular ultrasound. *J Am Coll Cardiol*. Jul. 5 2005; 46(1): 147-154; Mollet N R, Cademartiri F, Nieman K, et al. Multislice spiral computed tomography coronary angiography in patients with stable angina pectoris. *J Am Coll Cardiol*. Jun. 16 2004; 43(12):2265-2270). However, a number of studies have demonstrated that coronary atherosclerosis measurements by MDCTA are not highly predictive of ischemia (Hacker M, Jakobs T, Matthiesen F, et al. Comparison of spiral multidetector CT angiography and myocardial perfusion imaging in the noninvasive detection of functionally relevant coronary artery lesions: first clinical experiences. *J Nucl Med*. August 2005; 46(8):1294-1300; Rispler S, Keidar Z, Ghersin E, et al. Integrated single-photon emission computed tomography and computed tomography coronary angiography for the assessment of hemodynamically significant coronary artery lesions. *J Am Coll Cardiol*. Mar. 13 2007; 49(10):1059-1067; Schuijf J D, Wijns W, Jukema J W, et al. Relationship between noninvasive coronary angiography with multi-slice computed tomography and myocardial perfusion imaging. *J Am Coll Cardiol*. Dec. 19 2006; 48(12): 2508-2514). These observations have fueled the pursuit of hybrid imaging strategies that combine radionuclide myocardial perfusion imaging (MPI) with MDCTA. While promising, this approach is limited by higher radiation doses, imperfect co-registration of datasets, and the cost of hybrid imaging (Rispler S, Keidar Z, Ghersin E, et al. Integrated single-photon emission computed tomography and computed tomography coronary angiography for the assessment of hemodynamically significant coronary artery lesions. *J Am Coll Cardiol*. Mar. 13 2007; 49(10):1059-1067). Thus, it would be attractive if MDCT alone could provide both atherosclerosis and perfusion imaging in a single, self-registered exam.

However, accurate quantitative MPI using magnetic resonance or positron emission tomography (PET) rely heavily on the precise characterization of the arterial input function (AIF) or the arterial delivery of contrast/tracer to the myocardium (Christian T F, Rettmann D W, Aletras A H, et al. Absolute myocardial perfusion in canines measured by using dual-bolus first-pass MR imaging. *Radiology*. September 2004; 232(3):677-684; Jerosch-Herold M, Wilke N, Stillman AE. Magnetic resonance quantification of the myocardial perfusion reserve with a Fermi function model for constrained deconvolution. *Med Phys*. January 1998; 25(1):73-84; Schelbert H R, Phelps M E, Huang S C, et al. N-13 ammonia as an indicator of myocardial blood flow. *Circulation*. June 1981; 63(6):1259-1272). Likewise, previous studies using X-ray computed tomography have incorporated the AIF into the quantification of myocardial blood flow (MBF), but required dynamic CT imaging of the heart (Mohlenkamp S, Behrenbeck T R, Lerman A, et al. Coronary microvascular functional reserve: quantification of long-term changes with electron-beam CT preliminary results in a porcine model. *Radiology*. October 2001; 221(1):229-236; Rumberger J A, Feiring A J, Lipton M J, et al. Use of ultrafast computed tomography to quantitate regional myocardial perfusion: a preliminary report. *J Am Coll Cardiol*. January 1987; 9(1): 59-69; Wang T W X, Chung N, et al. Myocardial Blood Flow Estimated by Synchronous Multislice, High-Speed Computed Tomography. *IEEE Trans. Med. Imaging*. 1989 1989; 8:70-77; Wolfkiel C J, Ferguson J L, Chomka E V, et al. Measurement of myocardial blood flow by ultrafast computed tomography. *Circulation*. December 1987; 76(6):1262-1273; Wu X S, Ewert D L, Liu Y H, et al. In vivo relation of intramyocardial blood volume to myocardial perfusion. Evidence supporting microvascular site for autoregulation. *Circulation*. February 1992; 85(2):730-737). Together, these studies further illustrate that the accurate characterization of the AIF is essential to quantitative MPI.

Helical MDCT, unlike dynamic MDCT, acquires cardiac images over a short period of time (5-10 seconds) during peak contrast enhancement using a spiral mode of scanning. Due to the spiral nature of MDCTA acquisition, it is generally thought that information regarding contrast kinetics, such as the AIF, cannot be obtained. Interestingly, MDCTA imaging protocols actually do acquire image data that can be used to reconstruct the AIF according to embodiments of the current invention. Many MDCTA protocols use an automated bolus tracking method for triggering the appropriate time for helical MDCT scanning of the coronary arteries. Bolus tracking image data records the early part of contrast enhancement over time, data that is usually discarded following imaging. Additionally, helical MDCT images can be registered to the time of acquisition and can be used to construct the latter portion of the AIF according to embodiments of the current invention. Therefore, by combining the dynamic bolus tracking and time-registered helical MDCT image data sets, the time-attenuation curve of the AIF can be constructed according to embodiments of the current invention. There is thus a need for improved multi-detector computed tomography systems for combined myocardial perfusion imaging and the diagnosis of coronary artery disease.

SUMMARY

A computed tomography system according to an embodiment of the current invention has a support stage constructed and arranged to support a subject while under observation, an x-ray illumination system arranged proximate the support stage to illuminate the subject with x-rays, an x-ray detection system arranged proximate the support stage to detect x-rays after they pass through the subject and to provide signals based on the detected x-rays, and a data processing system in communication with the x-ray detection system to receive the signals from the x-ray detection system. The computed tomography system has a dynamic mode of operation in which the x-ray illumination system illuminates a portion of the subject a plurality of times and the data processing system processes at least some of the signals from the x-ray detection system to obtain a plurality of computed tomography images of the portion of the subject corresponding to the plurality of times to provide information regarding a change in the portion of the subject over the plurality of times. The computed tomography system also has a scanning mode of operation in which the x-ray illumination system illuminates a plurality of portions of the subject and the data processing system processes at least some of the signals from the x-ray detection system to obtain a plurality of computed tomography images of a corresponding plurality of portions of the subject to provide a substantially three-dimensional representation of an internal structure of the subject. The data processing system extracts information concerning a dynamic process of the subject based on signals from both the dynamic mode and the scanning mode of operation.

A method of processing x-ray signals according to an embodiment of the current invention include receiving signals detected from x-rays that have passed through a subject under observation during a dynamic mode of operation in which an x-ray illumination system illuminates a portion of the subject a plurality of times; processing the signals received from the dynamic mode of operation to obtain a plurality of computed tomography images of the portion of the subject corresponding to the plurality of times to provide information regarding a change in the portion of the subject over plurality of times; receiving signals detected from x-rays that have passed through the subject under observation during a scanning mode of operation in which the x-ray illumination system illuminates a plurality of portions of the subject; processing the signals received during the scanning mode of operation to obtain a plurality of computed tomography images of a corresponding plurality of portions of the subject to provide a substantially three-dimensional representation of an internal structure of the subject; and extracting information concerning a dynamic process of the subject from the processing the x-ray signals received during both the dynamic mode and the scanning mode of operation.

BRIEF DESCRIPTION OF THE DRAWINGS

The invention may be better understood by reading the following detailed description with reference to the accompanying figures, as follows:

FIG. 3A shows dynamic bolus tracking performed at the aortic root (green line) until a threshold of 180 Hounsfield units is reached. This is followed by a 3.6 second pause and the onset of helical imaging (blue lines). Each helical acquired slice is registered in time according to the equation given in the detailed description where $\Delta D$ is the change in distance in the z axis with respect to most cranial acquired axial slice, GRT is the gantry rotation time, ST is slice thickness, and HP is the helical pitch. FIG. 3B and FIG. 3C show the dynamic bolus tracking and helical MDCT image data reconstructed in the axial plane (FIG. 3B) and the arterial blood pool attenuation is measured during dynamic bolus tracking (left side) and in each helical MDCT image (right side). The attenuation density data are plotted over time and the arterial input function is reconstructed using dynamic bolus tracking and time-registered helical MDCT data, as well as the time-registered myocardial attenuation densities in the ischemic (right) and remote (middle) territories of FIG. 3C.

FIG. 4A demonstrates the actual arterial input function reconstructed from dynamic MDCT data. FIG. 4B shows the reconstructed arterial input function from the combination of dynamic bolus tracking and time-registered helical MDCT data. The dashed line in FIG. 4B represents interpolated data during the pause in imaging between dynamic bolus tracking and time-registered helical imaging. Data shown were normalized by subtracting the baseline attenuation density prior to contrast arrival from all measurements.

FIG. 5A demonstrates the agreement between the two methods when using the area under the curve (AUC) of the entire AIF. FIG. 5B demonstrates the agreement when using the AUC of the AIF during helical imaging only.

FIGS. 7A-7D display the following metrics compared with myocardial blood flow: myocardial attenuation density, myocardial attenuation density (AD) ratio, myocardial/entire area under the curve (AUC) ratio, and the myocardial/helical AUC ratio; respectively.

DETAILED DESCRIPTION

Figure 1:
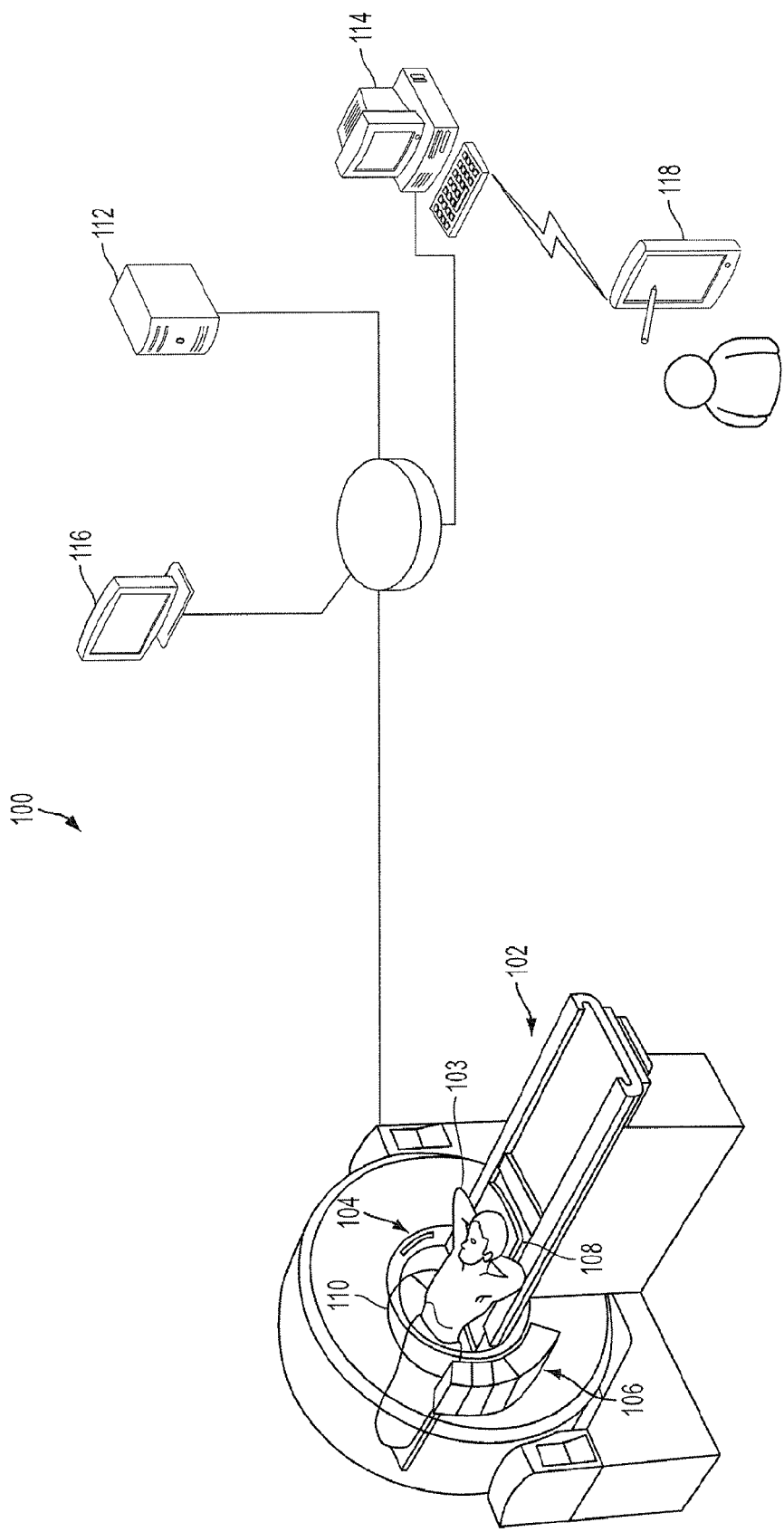
FIG. 1 is a schematic illustration of a computed tomography system according to an embodiment of the current invention.

In describing embodiments of the present invention illustrated in the drawings, specific terminology is employed for the sake of clarity. However, the invention is not intended to be limited to the specific terminology so selected. It is to be understood that each specific element includes all technical equivalents which operate in a similar manner to accomplish a similar purpose.

Throughout this specification, various terms and abbreviations are used. The following lists various abbreviations and acronyms together for convenience:
HU=Hounsfield units;
LAD=left anterior descending artery;
MBF=myocardial blood flow;
MDCTA=multi-detector computed tomography angiography;
MPI=myocardial perfusion imaging;
PET=positron emission tomography;
AD=attenuation density;
SPECT=single photon emission computed tomography;
AIF=Arterial input function;
LV=Left ventricle/ventricular;
AUC=Area under the curve; and
GRT=Gantry rotation time.

FIG. 1 is a schematic illustration of a computed tomography system 100 according to an embodiment of the current invention. The computed tomography system 100 includes a support stage 102 constructed and arranged to support a subject 103 while under observation, an x-ray illumination system 104 arranged proximate the support stage 102 to illuminate the subject 103 with x-rays, and an x-ray detection system 106 arranged proximate the support stage 102 to detect x-rays after they pass through the subject 103 and to provide signals based on the detected x-rays. In some embodiments, the x-ray detection system can be an array of detectors, such as in multi-detector computed tomography (MDCT) systems. The support stage 102 can be an assembly that has a top portion 108 that can slide the subject 103 back and forth along a longitudinal direction as illustrated in FIG. 1. However, general concepts of the current invention are not limited to such a structure. The x-ray illumination system 104 and the x-ray detection system 106 can be rotatably mounted on a gantry 110 in some embodiments of the current invention. In this embodiment, the gantry 110 can be rotated to thereby rotate the x-ray illumination system 104 and x-ray detection system 106 to generate signals that can be processed to obtain an x-ray image for a cross sectional slice of the subject 103. The subject 103 can be moved to a new position relative to the gantry 110 in order to obtain an x-ray image of another slice of the subject 103. However, the general concepts of the current invention are not limited to this particular mechanical arrangement. Other mechanical arrangements to selectively move the x-range illumination system and x-ray detection system relative to the subject may be used in other embodiments. Furthermore, non-mechanical beam steering approaches could also be used in some embodiments.

The computed tomography system 100 also includes a data processing system 112 that is in communication with the x-ray detection system 106 to receive the signals from the x-ray detection system 106. The data processing system 112 is implemented on a networked computer in this example. However, the data processing system could also be included locally within a structure that includes the x-ray detection system 106 and/or may be a personal computer 114, and/or any other suitable data processing systems. The computed tomography system 100 can also include data storage within any of the computer systems and/or other data storage peripheral devices attached or networked, as desired. In addition, the computed tomography system 100 can also include various input/output devices and can include a display system 116, for example. In other embodiments, the computed tomography system 100 can include various handheld devices, such as hand held device 118. In this example, the handheld device has wireless communications within the computed tomography system 100. Although other components are illustrated as being networked together with physical connections, such as electrical or fiber optic cables, they could also be networked with wireless connections.

The data processing system 112 can be programmed and/or hard wired to perform the computational tasks of the computed tomography system 100, which can include image processing to generate x-ray images, for example. The computed tomography system 100 has a dynamic mode of operation in which the x-ray illumination system 104 illuminates a portion of the subject 103 a plurality of times and the data processing system 112 processes at least some of the signals from the x-ray detection system 106 to obtain a plurality of computed tomography images of the portion of the subject corresponding to the plurality of times. The data processing system 112 can then obtain information regarding a change in the portion of the subject 103 over the plurality of times based on the plurality of computed tomography images. For example, in one embodiment, this can include bolus tracking in which a contrast agent is injected into the subject 103. The computed tomography system 100 can then obtain multiple images at successive times of the same x-ray slice in order to observe changes in time while the slice remains substantially constant with respect to the subject 103.

The computed tomography system 100 also has a scanning mode of operation in which the x-ray illumination system 104 illuminates a plurality of portions of the subject 103 and the data processing system 112 processes at least some of the signals from the x-ray detection system 106 to obtain a plurality of computed tomography images of a corresponding plurality of portions of the subject 103. The plurality of computed tomography images can provide a substantially three-dimensional representation of an internal structure of the subject 103, for example. In one example according to the embodiment of FIG. 1, the top portion 108 of the support stage 102 can be moved in the axial (longitudinal) direction as the x-ray illumination system 104 and x-ray detection system 106 rotate with the gantry 110 so as to trace out a helical, or spiral, illumination path over a portion of the subject 103.

The data processing system 112 also extracts information concerning a dynamic process of the subject 103 based on signals from both the dynamic mode and the scanning mode. In some embodiments of the current invention, the data processing system can determine at least an approximation to an arterial input function of the subject 103 based on information obtained from processing the signals from the x-ray detection system during both the dynamic and scanning modes of operation. In addition, there can be a pause time between the dynamic and scanning modes of the computed tomography system 100. This can be the case in order to reduce the cost, size and complexity of the x-ray illumination and detection systems, for example. In some embodiments, the pause time is taken into account during the processing by the data processing system 112, for example, in the determination of the arterial input function. In some embodiments, the pause time can be reduced to less than about 5 seconds. In some embodiments, the pause time can be reduced to less than about 3.5 seconds. And, in some embodiments the pause time can be eliminated.

In some embodiments, the data processing system 112 can extract the information concerning the dynamic process of the subject 103 such that times corresponding to each of the plurality of computed tomography images during the dynamic mode are related to times of each of the plurality of computed tomography images of the corresponding plurality of portions of the subject 103. For example, the image slices obtained at different positions of the subject 103 can each be assigned a time of observation. Based on the time of observation of each slice, both from the dynamic and scanning modes, time-dependent information of the subject 103 can be obtained. The time of observation for each image slice taken during a helical scan mode, according to some embodiments of the current invention, can be determined based on system parameters. For example, times of each of said plurality of computed tomography images can be determined based on the formula $$\text{Time(Secs)} = \frac{\Delta D \cdot GRT}{ST \cdot HP},$$

where Time is the mean time in seconds of image acquisition, $\Delta D$ is the change in distance in a longitudinal axis with respect to a most cranial acquired axial slice, GRT is the gantry rotation speed, ST is the image slice thickness, and HP is the helical pitch.

Figure 1A:
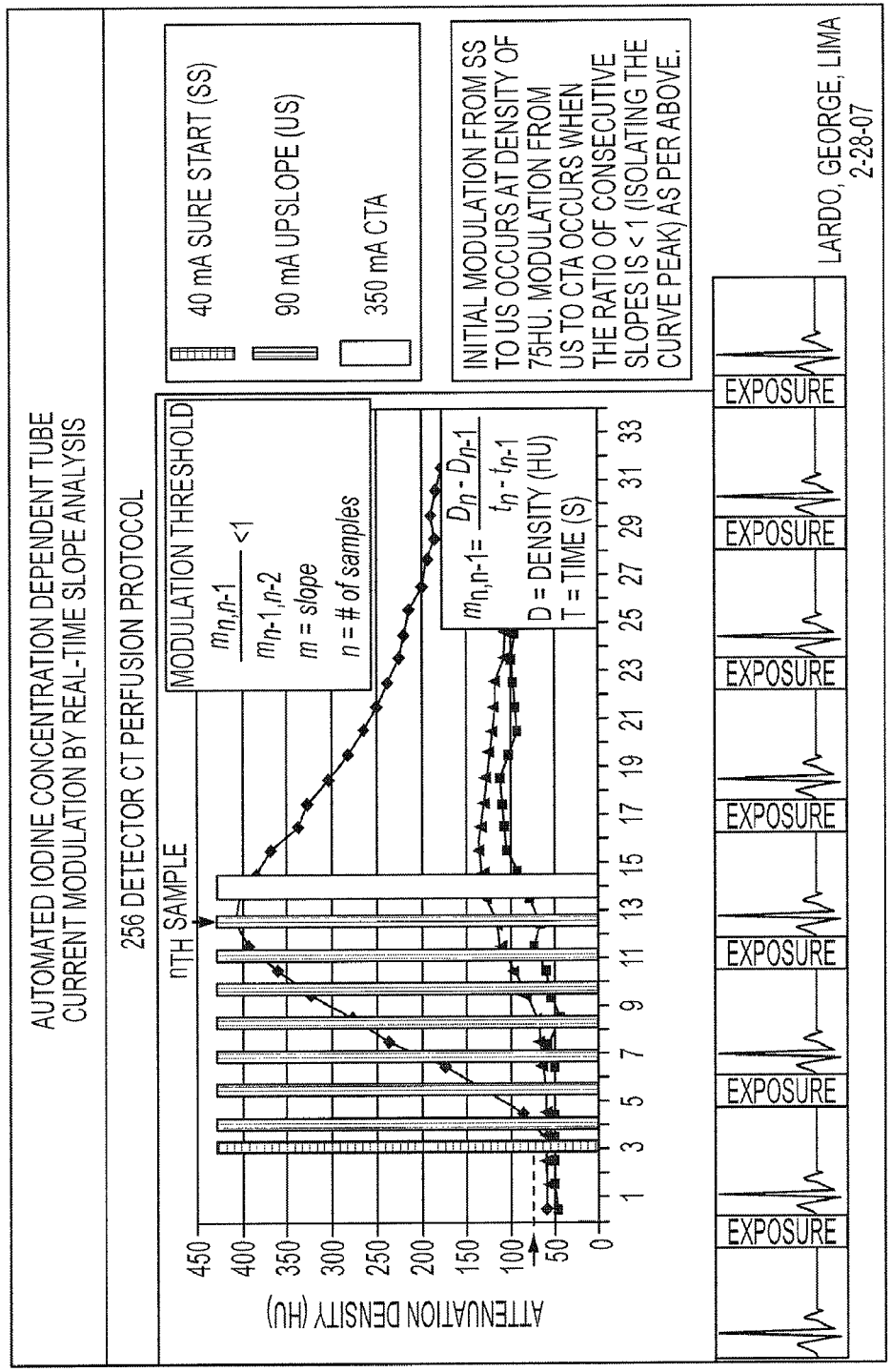
FIG. 1A is an illustration to help explain a computed tomography system according to an embodiment of the current invention which has a non-helical scanning mode of operation.

In addition, in the case of non-helical imaging where partial or full cardiac coverage can be obtained at one or several time points, the time of image slice acquisition may be derived from the actual time of acquisition and the above equation may not be needed. Some recent scanners do not use helical imaging and instead use a step and shoot method. For example, instead of continuous table movement, the table may move at set intervals (every other heart beat). A picture is taken during one heart beat, the table moves on the next heart beat, and the next picture is taken. Also, even more recently, some scanners take a picture in a single heart beat and cover the whole heart in this single heart beat. Therefore, there would only be one time point. The general concepts of this invention are not limited to a specific scanning method. FIG. 1A shows an example of a non-helical scanning approach according to an embodiment of the current invention.

EXAMPLES

Purposes of this example are to: 1) validate a novel MDCT myocardial perfusion acquisition and analysis method that allows for the reconstruction of the AIF from the combination of dynamic bolus tracking data and helical MDCT time-registered data according to an embodiment of the current invention, and 2) determine if normalization of myocardial attenuation values by the reconstructed AIF improves the assessment of MBF measurements during first-pass, contrast-enhanced adenosine stress MDCT in a canine model of left anterior descending (LAD) artery stenosis.

Methods

Animal preparation. The Animal Care and Use Committee of the Johns Hopkins University School of Medicine approved all procedures. A total of eleven mongrel dogs (24.5-29.5 kg) were anesthetized with intravenous thiopental, intubated, and mechanically ventilated with isoflurane anesthesia during preparation and MDCT scanning. Following femoral cut downs, 8F sheaths were placed in both femoral veins, right femoral artery, and the right internal jugular vein.

Four normal canines were prepared for validation of the proposed method as described in Part A below. Following validation, the reconstructed AIF method was incorporated into perfusion measurements made in seven canine models of coronary ischemia as described in Part B.

Part A
Arterial Input Function Reconstruction Validation Studies

To validate that the AIF derived from the combination of bolus tracking and time-registered helical imaging can accurately reconstruct the actual AIF, four animals underwent sequential bolus tracking and helical imaging followed by dynamic MDCT imaging alone (gold standard for AIF). Each animal was placed in a 64-detector MDCT scanner (Aquilion 64, Toshiba Medical Systems, Otawara, Japan) and attached to an ECG monitor. Both scans were performed with intravenous iodinated contrast infused at a rate of 4 ml/sec for 16 ml via the right internal jugular venous catheter, followed by a 4 ml/sec infusion of a 30%/70% mixture of contrast and normal saline for 40 ml, followed by a saline infusion 4 ml/sec×50 ml. Each scan was separated by 10 minutes. All scanning was performed with respiration suspended. A detailed description of each protocol is below.

Scan 1—Combined Dynamic Bolus Tracking/Helical MDCT Imaging

Figure 2:
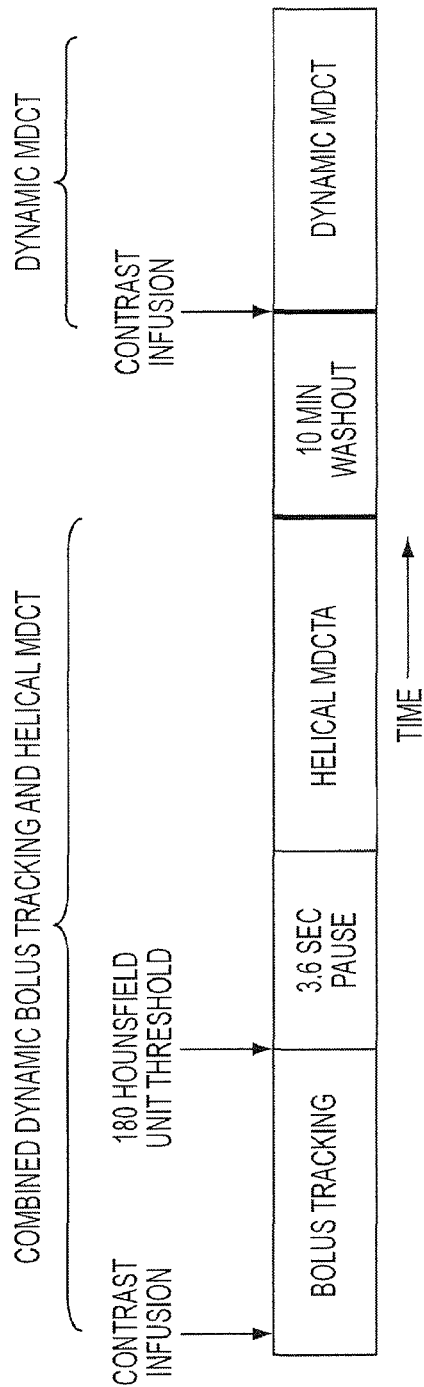
FIG. 2 shows a timeline diagram for the arterial input function comparison for a particular example according to an embodiment of the current invention. Bolus tracking imaging began in tandem with the first infusion of iodinated contrast. When a threshold of 180 Hounsfield units was detected in the ascending aorta, imaging paused for 3.6 seconds and helical MDCT imaging started. Ten minutes following the combined bolus tracking and time-registered helical MDCT imaging, contrast was again infused and dynamic MDCT imaging was performed to record the actual arterial input function.

Image Acquisition—Bolus tracking imaging was performed at the aortic root level and initiated at the onset of contrast infusion (see above) using following protocol: gantry rotation time=400 ms, detector collimation=0.5 mm×4, tube voltage=120 kV, tube current=70 mA, and a display field of view=160 mm. Once a threshold of 180 Hounsfield units (HU) was detected in the aortic root, there was a 3.6 second pause in imaging followed by helical MDCT imaging using a retrospectively gated MDCT coronary angiography protocol with the following parameters: gantry rotation time=400 ms, detector collimation=0.5 mm×64, helical pitch=variable depending on heart rate (range: 14.4-16.2), beam pitch=variable depending on heart rate (range: 0.224-0.275), tube voltage=120 kV, tube current=400 mA, and a display field of view=160 mm. Imaging started at the aortic root and stopped caudal to all cardiac structures. The 3.6 second pause between the end of dynamic bolus tracking and the onset of helical imaging is required according to this embodiment for changing of tube current and movement of the collimators. See timeline, FIG. 2.

Figure 3A:
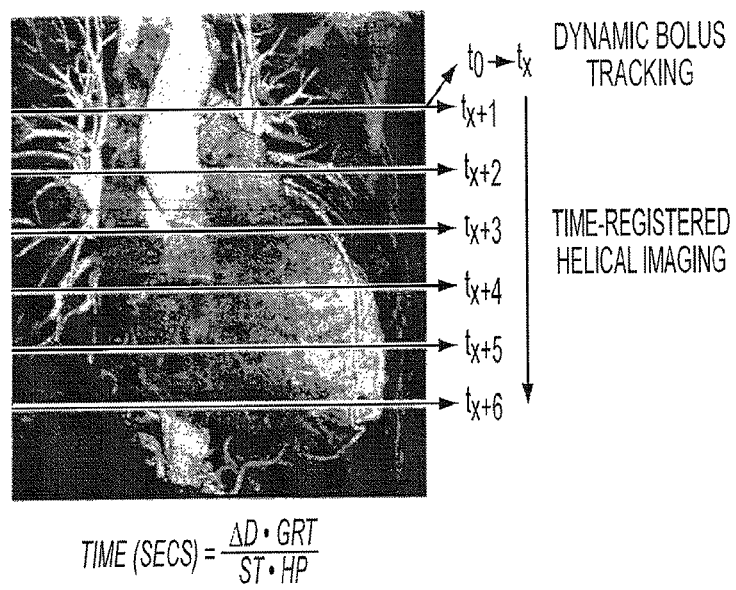
FIGS. 3A-3C show a simulation of the arterial input function using combined dynamic bolus tracking and time-registered helical MDCT.
Figure 3B:
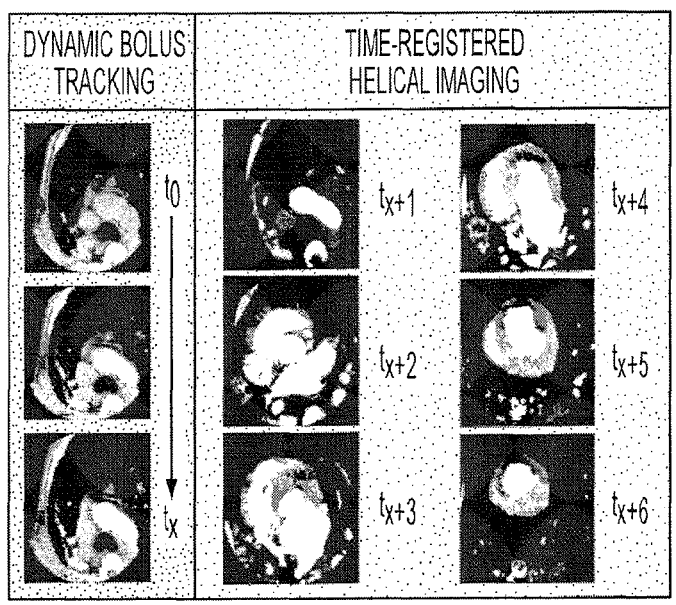
Figure 3C:
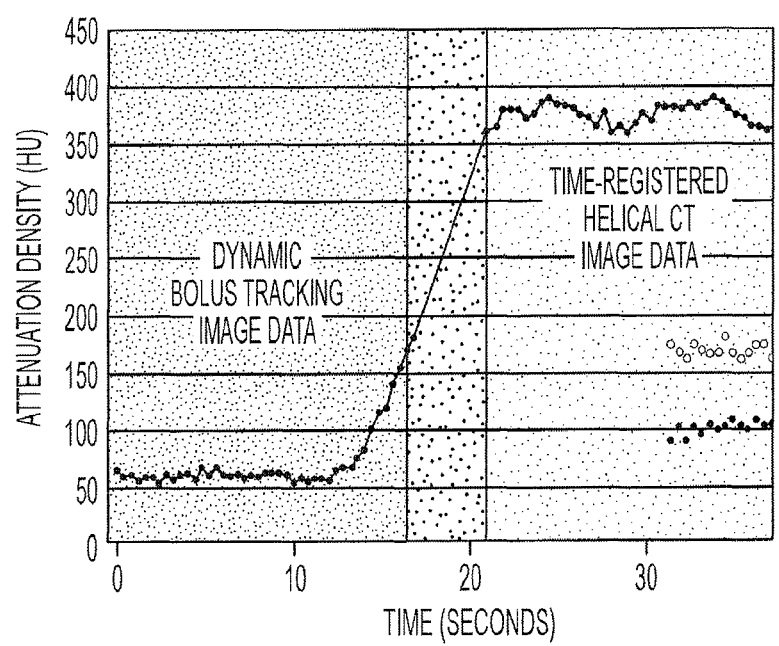

Image Reconstruction and Analysis—In order reconstruct the AIF from bolus tracking and time-registered helical, the following method was implemented:

1) Bolus tracking data acquired as part of the helical exam was reconstructed at 0.4 second intervals, a 2 mm slice thickness, and using a standard MDCTA convolution kernel (FC43). A region of interest was drawn in the aortic root and the mean attenuation density (AD) in HU of each image was calculated over time. Using this data, a time-attenuation curve of early portion of the AIF was reconstructed (see FIGS. 3A-3C).

2) Helical MDCT images were reconstructed at a cardiac phase of 80%, using a standard MDCTA convolution kernel (FC43), and a slice thickness of 4 mm. A region of interest was drawn in the intravascular blood pool of each image beginning in the aortic root, throughout the left ventricular (LV) blood pool and ending at LV apex and the mean AD in HU was calculated for the intravascular blood pool in each axial slice. With knowledge of slice position, with respect to the most cranial slice, slice thickness, helical pitch and gantry rotation time; each image in the axial plane was assigned a mean time of image acquisition from the initiation of helical imaging according to the following equation:

$$\text{Time(Secs)} = \frac{\Delta D \cdot GRT}{ST \cdot HP}$$

Where time is the mean time in seconds of image acquisition, ΔD is the change in distance in the z axis with respect to most cranial acquired axial slice, GRT is the gantry rotation speed, ST is slice thickness, and HP is the helical pitch. Using the mean AD of each slice and its time of acquisition with respect to the bolus tracking imaging, the latter part of the time-attenuation curve was constructed, see FIGS. 3A-3C.

3) Time-attenuation data from bolus tracking and time-registered helical MDCT imaging were combined, taking into account the 3.6 second pause between the two imaging modes. Each time-attenuation curve was baseline corrected by subtracting the baseline AD of the intravascular blood pool (prior to contrast arrival) from the measured AD. The reconstructed AIF was then characterized using 2 methods: a) The area under the curve (AUC) of the entire reconstructed AIF was calculated from the time contrast first arrived in the ascending aorta to the time helical MDCT imaging ended and b) the AUC of the reconstructed AIF during helical imaging only was calculated.

Scan 2—Dynamic MDCT Imaging (Gold Standard)

Image Acquisition—Ten minutes following combined bolus tracking and helical MDCT imaging, iodinated contrast was infused and dynamic MDCT imaging was performed with the detectors aligned over the aortic root and aortic arch using the following protocol: gantry rotation time=400 ms, detector collimation=8 mm×4, no table movement, tube voltage=120 kV, tube current=400 mA, and a display field of view=160 mm. Continuous serial imaging of the first pass of the contrast bolus was performed for 60 seconds. See timeline, FIG. 2.

Image Reconstruction and Analysis—Dynamic MDCT images were reconstructed at 0.4 second intervals, 8 mm slice thickness, and using a standard MDCTA convolution kernel (FC43). Using hand planimetry, a region of interest was drawn in the ascending aorta, just cranial to the coronary ostia. The mean AD in the aortic blood pool was measured in each image and plotted over time. All measurements were baseline corrected by subtracting the measured baseline aortic blood pool AD (prior to contrast arrival in the aorta) from the measured AD. The AUC of the AIF was calculated using the same amount of imaging time from the combined bolus tracking and helical MDCT imaging. Therefore the AUC of the AIF was calculated beginning at the time contrast first arrived in the ascending aorta and up to the time required to complete the previous bolus tracking and helical MDCT scan.

Part B

Implementation of the Reconstructed Arterial Input Function for Helical MDCT Perfusion Imaging Experimental Preparation—In order to determine the added value a reconstructed AIF has on helical MDCT myocardial perfusion imaging, we tested the method utilizing a canine model of coronary artery stenosis. Following intubation, anesthesia, and vascular access as described above; seven canine models of LAD stenosis were prepared as follows: A left thoracotomy was performed in the fifth intercostal space and the pericardium was excised. A catheter was placed in the left atrium via the left atrial appendage for microsphere injections and a second catheter was then placed into the proximal descending aorta for microsphere sampling. The proximal to mid LAD was isolated and instrumented with an electromagnetic flow meter and reactive hyperemia was tested in the vessel with an inflatable external occluder. Suture was then secured around the LAD immediately distal to the electromagnetic flow meter and tightened to produce a graded stenosis aimed to maintain baseline flow, but attain a 50% or more reduction in hyperemic flow. The thoracotomy was closed, the pleural space was evacuated of all air, and the animal was transported to the MDCT suite using a portable ventilator.

Image Acquisition—Each animal was placed on an electrocardiographic monitor in a 64 detector MDCT scanner (Aquilion™ 64-Toshiba Medical Systems Corporation, Otawara, Japan). Animals received intravenous propranolol (5-20 mg) to achieve a heart rate <100 beats per minute. In order to study a wide range of flows, adenosine was infused via the left internal jugular venous sheath for 5 minutes at 0.14 mg/kg/min in three experiments, 0.21 mg/kg/min in three experiments and one animal did not receive adenosine. After scout film acquisition, intravenous contrast, iodixanol (Visipaque™ 320 mg iodine/ml—Amersham Health, Amersham, UK), was infused at a rate of 2.5 ml/sec for a total of 100 ml. Bolus tracking images were obtained using the following protocol: gantry rotation time=400 ms, detector collimation=0.5 mm×4, tube voltage=120 kV, tube current=70 mA, and a display field of view=13.2 cm. MDCT scanning was initiated when a threshold of 180 HU was detected in the ascending aorta. Respiration was then suspended with the airway open to air and imaging performed using a retrospectively gated MDCT protocol with the following parameters: gantry rotation time=400 ms, detector collimation=0.5 mm×32, pitch=variable depending on heart rate (range: 0.224-0.275), tube voltage=120 kV, tube current=400 mA, and a display field of view=13.2 cm. Imaging started at the aortic root and stopped caudal to all cardiac structures. Prior to discontinuation of the adenosine infusion, 7.5 million neutron-activated microspheres (Biopal, Inc, Worchester, Mass.) were injected to document MBF during adenosine infusion. Microsphere sampling rate from the descending aorta was 2.1 ml/minute.

Sample Processing—Following imaging, the animal was euthanized with a saturated solution of potassium chloride and the heart was excised and divided into five equal slices perpendicular to the short axis. Myocardial samples (0.87-3.24 g) were excised and microsphere myocardial blood flows were calculated according to the technique described by Reinhardt, et al (Reinhardt C P, Dalhberg S, Tries M A, et al. Stable labeled microspheres to measure perfusion: validation of a neutron activation assay technique. *Am J Physiol Heart Circ Physiol*. January 2001; 280(1):H108-116) from the anterior, anteroseptal, inferolateral, inferior and inferoseptal walls from base to apex according to the 17-segment system recommended by the American Heart Association Writing Group on Myocardial Segmentation and Registration for Cardiac Imaging (Cerqueira M D, Weissman N J, Dilsizian V, et al. Standardized myocardial segmentation and nomenclature for tomographic imaging of the heart: a statement for healthcare professionals from the Cardiac Imaging Committee of the Council on Clinical Cardiology of the American Heart Association. *Circulation*. Jan. 29 2002; 105(4):539-542).

Image Reconstruction and Analysis—Bolus tracking and helical MDCT images were reconstructed as described above in Part A and the reconstructed AIF was reconstructed using the combined bolus tracking and helical MDCT image data. The AUC of the reconstructed AIF was calculated using the two methods described above: a) using the entire AUC of the reconstructed AIF and b) using the AUC during helical imaging only.

Myocardial Attenuation Density Analysis—Using custom perfusion software (CineTool, GE Medical Systems), endocardial and epicardial borders were defined using an automated border detection algorithm with manual adjustments as needed. Using hand planimetry as previously described (George R T, Silva C, Cordeiro M A, et al. Multidetector computed tomography myocardial perfusion imaging during adenosine stress. *J Am Coll Cardiol.* Jul. 4 2006; 48(1):153-160), the remote myocardial AD and its standard deviation was determined on a slice-by-slice basis from base to apex in the inferoseptal, inferior, and inferolateral myocardial walls. These results were used to define a perfusion deficit AD threshold as myocardium having an AD one standard deviation below the mean AD of the remote region. The perfusion deficit threshold was entered into the software and the mean AD of the perfusion deficit in the anterior, anteroseptal, and anterolateral walls was determined from base to apex.

Myocardial Perfusion Metrics—In order to normalize the myocardial AD for the AIF, several methods were implemented:

Myocardial AD Ratio—The myocardial AD ratio was calculated by dividing the mean measured myocardial AD in remote and stenosed territories by the overall mean LV blood pool AD as previously described (George R T, Silva C, Cordeiro M A, et al. Multidetector computed tomography myocardial perfusion imaging during adenosine stress. *J Am Coll Cardiol.* Jul. 4 2006; 48(1):153-160):

$$\text{Myocardial } AD \text{ Ratio} = \frac{\text{Mean } MYO_{AD}}{\text{Mean } LV_{AD}}$$

($MYO_{AD}$=myocardial attenuation density, $LV_{AD}$=left ventricular blood pool attenuation density).

Myocardial/Entire AUC Ratio—In order to normalize the myocardial AD by the entire AIF curve, the measured myocardial AD were divided by the AUC of the entire reconstructed and interpolated AIF:

$$\text{Myocardial/Entire } AUC \text{ Ratio} = \frac{\text{Mean } MYO_{AD}}{\text{Entire } AUC}$$

($MYO_{SD}$=myocardial attenuation density, Entire AUC=area under the curve of the entire reconstructed and interpolated arterial input function).

Myocardial/Helical AUC Ratio—In order to normalize the myocardial AD by the portion of the AIF curve measured during helical imaging only, the myocardial AD was divided by the AUC of the AIF that was acquired during helical imaging as follows:

$$\text{Myocardial/Helical } AUC \text{ Ratio} = \frac{\text{Mean } MYO_{AD}}{\text{Helical } AUC}$$

($MYO_{AD}$=myocardial attenuation density, Helical AUC=area under the curve of the arterial input function acquired during the helical scan).

Each of the myocardial metrics above was measured in the perfusion deficit and remote myocardium and were directly compared with microsphere derived MBF (gold standard) over the range of flows studied.

Statistical Analysis—Microsphere MBF and myocardial AD were expressed as mean±standard deviation. Mean microsphere MBF and MDCT perfusion metrics were compared using the paired t-test. Relationships between myocardial perfusion metrics and microsphere MBF were examined using linear regression. Regression analyses accounted for multiple measures clustered in each experiment such that measurements were considered independent across dogs, but not within dogs (Williams R L. A note on robust variance estimation for cluster-correlated data. *Biometrics.* June 2000; 56(2):645-646). All tests were performed at an alpha level of p<0.05. Statistical analyses were performed using Stata, Version 7, College Station, Tex.

Results

Part A—Validation Studies

Reconstructed vs. Actual Dynamic Arterial Input Function

Figure 4A:
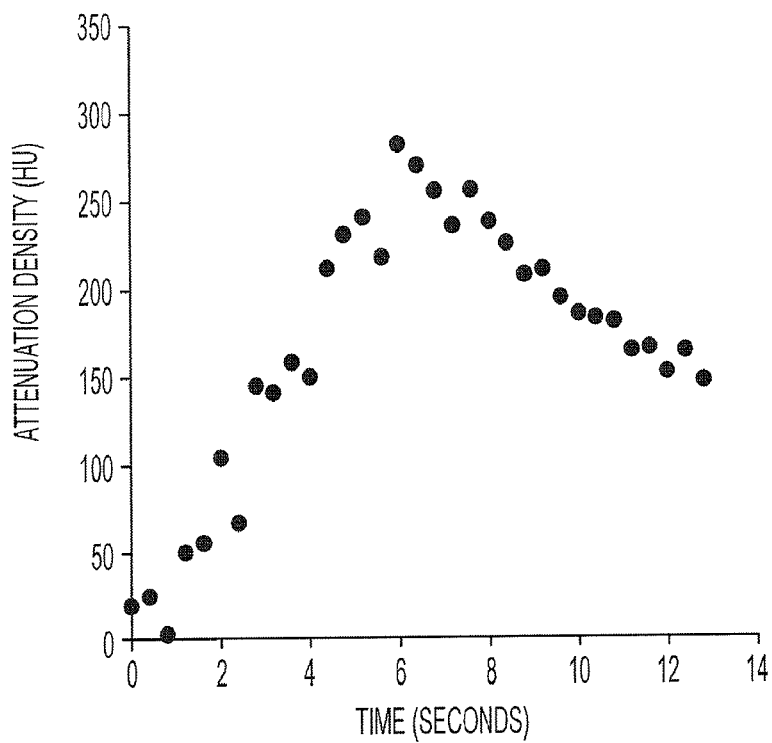
FIGS. 4A and 4B show a comparison of the arterial input function derived from two methods.
Figure 4B:
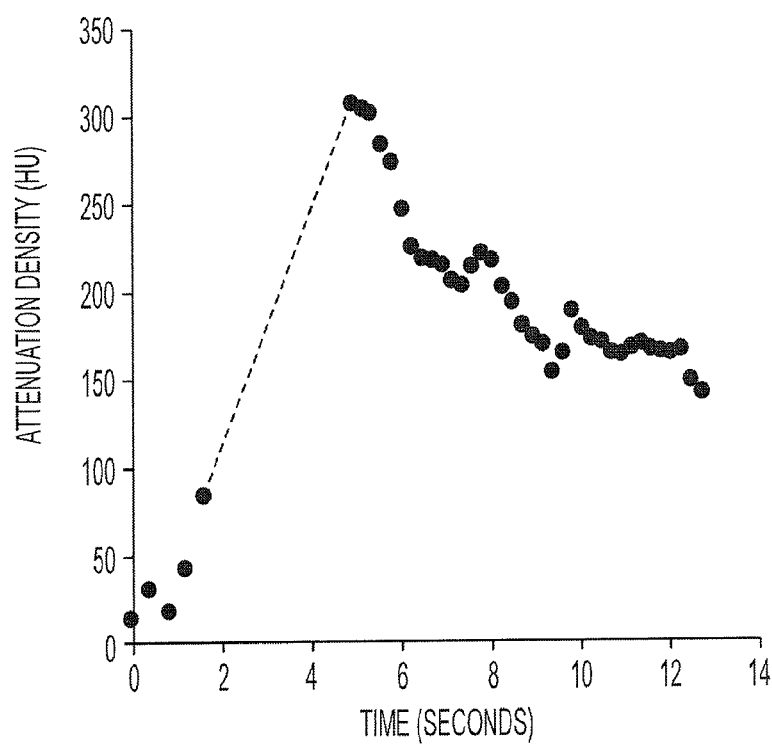
Figure 5A:
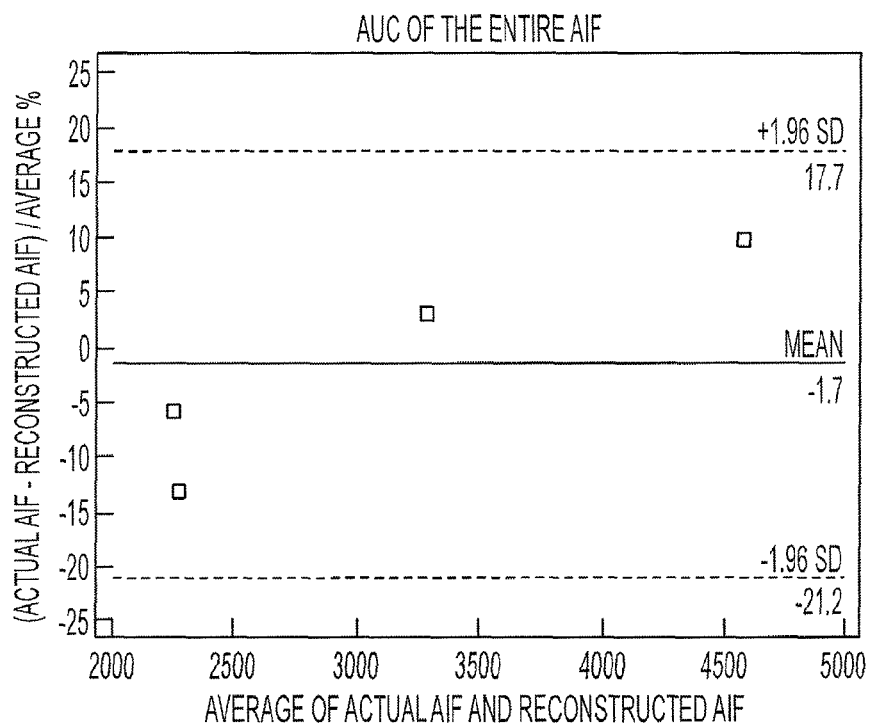
FIGS. 5A and 5B show Bland-Altman plots comparing the actual arterial input function (AIF) from dynamic MDCT imaging (actual AIF) to the AIF from combined dynamic bolus tracking and time-registered helical MDCT (reconstructed AIF).
Figure 5B:
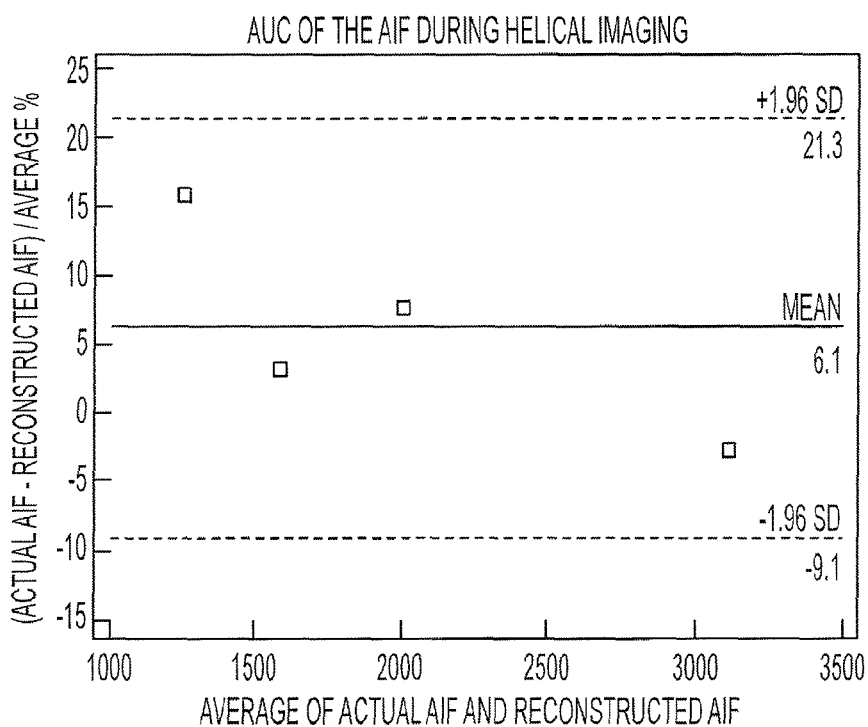

Four animals underwent combined bolus tracking and time-registered helical MDCT imaging followed by dynamic MDCT imaging. The AIF derived from dynamic MDCT (gold standard) compared with combined bolus tracking and time-registered helical MDCT is displayed in FIGS. 4A and 4B. When considering the entire AIF, the AUC was 3,108±1, 250 vs. 3,086±941 when comparing the actual AIF from dynamic MDCT and the reconstructed AIF from combined dynamic bolus tracking and time-registered helical MDCT, respectively, with a mean percent difference of 1.7% (p=0.90), FIG. 5A. When considering the AIF measured during helical imaging only, the AUC was 2027±759 vs. 1945±863 when comparing actual vs. the reconstructed AIF, respectively with a mean percent difference of 6.1% (p=0.27), FIG. 5B.

Part B—Implementation Studies

Myocardial Perfusion Metrics

Figure 6:
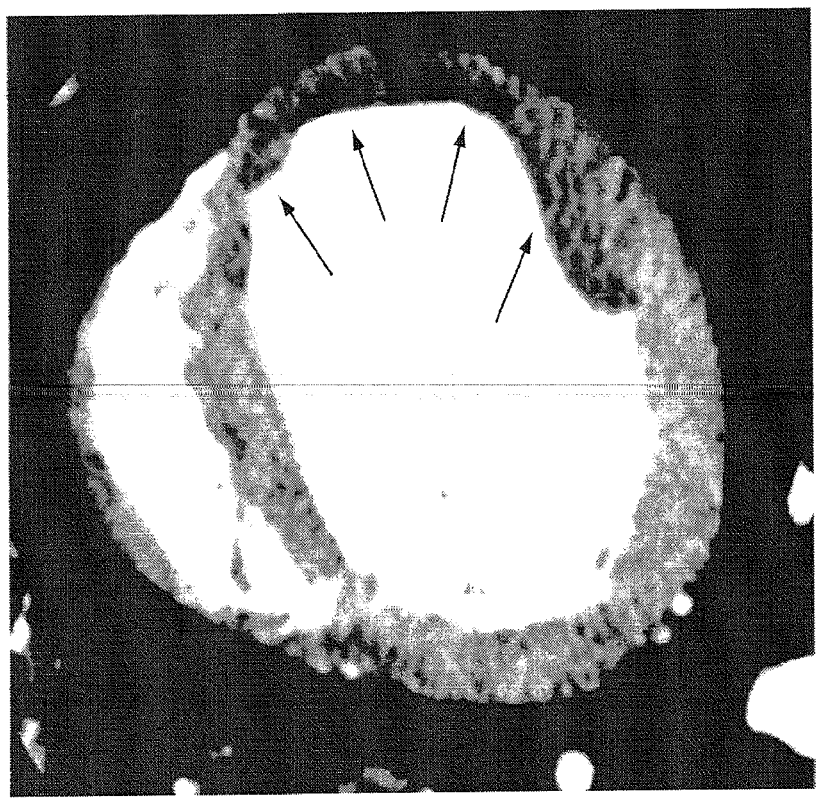
FIG. 6 is an adenosine-stress MDCT perfusion image; mid-ventricular myocardial slice in the axial plane acquired during adenosine stress MDCT in a canine model of left anterior descending artery stenosis. Note the subendocardial perfusion deficit in the anteroseptal, anterior, and anterolateral walls. The microsphere myocardial blood flow in stenosed territory (anterior) and remote territory was 1.9 ml/g/min and 9.8 ml/g/min, respectively.
Figure 7A:
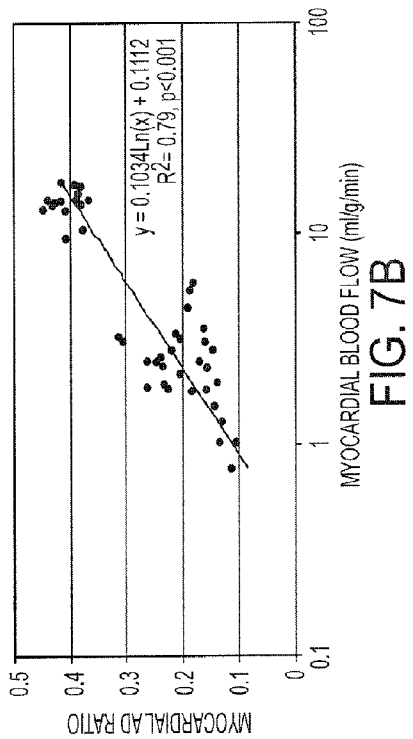
FIGS. 7A-7D show MDCT derived perfusion metrics (y-axis) compared with microsphere myocardial blood flow (x-axis).

Seven animals underwent adenosine stress MDCT MPI. However, the onset of helical imaging was delayed in one animal due to technical error and this animal was excluded from the analysis. During adenosine infusion, microsphere MBF was 2.4±0.8 ml/g/min in stenosed vs. 10.2±6.3 ml/g/min in remote territories (p<0.001). Perfusion deficits showed differences in myocardial AD compared with remote regions on visual inspection (FIG. 6). Myocardial perfusion metric measurements are summarized in Table 1. Defect size, expressed as a percentage of total myocardium was 16.2%±8.9. Myocardial AD measured 104±32 HU vs. 161.4±40 HU in stenosed vs. remote territories, respectively (p<0.001). There was a moderate relationship between myocardial AD without AIF normalization vs. microsphere derived MBF (y=43.117 Ln(x)+71.705, $R^2$=0.75, p=0.003) (see FIG. 7A).

Figure 7B:
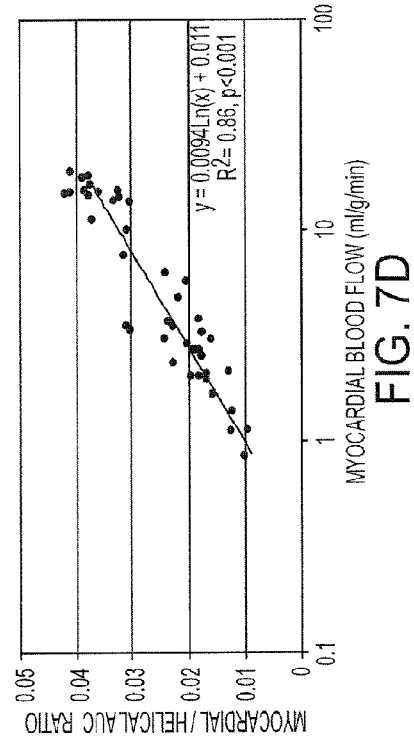

Myocardial AD Ratio—The ratio of the myocardial AD and the LV cavity blood pool AD (Mean $MYO_{AD}$/Mean $LV_{AD}$), was 0.20±0.07 for stenosed vs. 0.31±0.11 for remote territories (p<0.001). There was a significant non-linear relationship between the AD ratio (Mean $MYO_{AD}$/Mean $LV_{AD}$) and microsphere MBF over the entire range of flows studied (y=0.1034 Ln(x)+0.1112, $R^2$=0.79, p<0.001) (FIG. 7B).

Figure 7C:
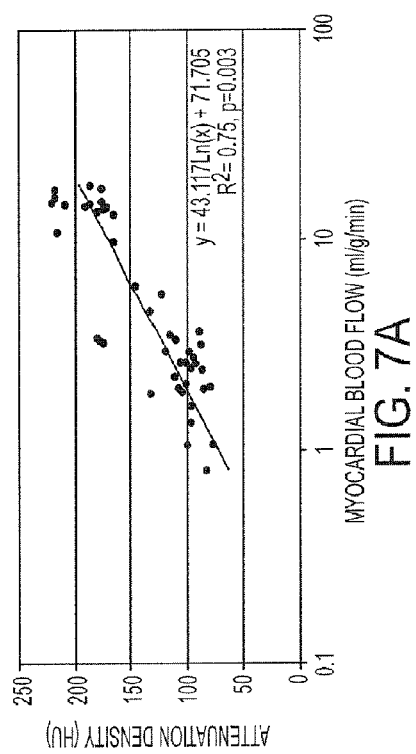

Area Under the Entire Arterial Input Function Curve—When using the AUC of the entire AIF curve, the Mean $MYO_{AD}$/Entire AUC ratio was 0.015±0.004 in the stenosed vs. 0.023±0.006 in the remote territories (p<0.001). There was a significant non-linear relationship between the Mean $MYO_{AD}$/Entire AUC ratio and microsphere derived MBF (y=0.0061 Ln(x)+0.0099, $R^2$=0.82, p<0.001) (FIG. 7C).

Figure 7D:
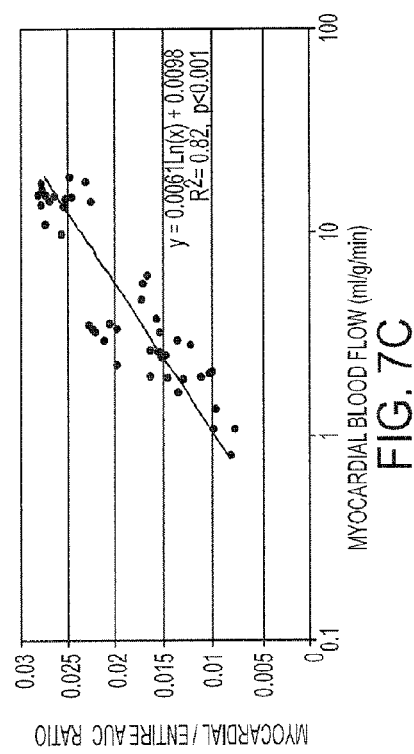

Area Under the Arterial Input Function Curve Measured During the Helical Acquisition—When using the AUC of the portion of the AIF that was acquired during helical imaging, the Myocardial/Helical AUC ratio was 0.019±0.006 in the stenosed vs. 0.030±0.009 in the remote territories (p=0.001). The Myocardial/Helical AUC ratio had the best curvilinear agreement with microsphere derived MBF (y=0.0094 Ln(x)+0.011, $R^2$=0.86, p<0.001) (FIG. 7D).

Discussion

Main Findings

The main findings of this example are: 1) first-pass, contrast enhanced helical MDCT imaging when combined with bolus tracking imaging data can characterize the AIF and 2) MDCT myocardial attenuation densities, when normalized to several AIF metrics correlate well with microsphere derived MBF. These data are the first to demonstrate that time-registered CT attenuation data can be extracted from helical imaging protocols designed for first-pass coronary angiography and that this time-registered attenuation data can be used to better characterize the AIF, thus improving the measurement myocardial perfusion using helical MDCT methods.

Myocardial Perfusion Imaging: Importance of the Arterial Input Function

Our study used a novel method to characterize the AIF with the goal of improving the accuracy of myocardial perfusion imaging using MDCT. The AIF physically represents the amount and rate of contrast delivery to the myocardium and is influenced by factors such as the rate of contrast injection, the overall dose of contrast, peripheral and pulmonary venous flow, and cardiac output. Accurate measurement of the AIF is essential for all modalities that seek to quantify MBF.

Radionuclide MPI is well established for the evaluation of myocardial perfusion. However, SPECT MPI and PET using rubidium-82 (most often, clinically) rely on relative differences in myocardial uptake of the tracer and do not use the AIF in the measurement of MBF. Accordingly, these techniques are qualitative or semi-quantitative at best. On the other hand, Nitrogen-13 PET, which utilizes the AIF, can quantify absolute MBF up to 2.0-2.5 ml/g/min (Schelbert H R, Phelps M E, Huang S C, et al. N-13 ammonia as an indicator of myocardial blood flow. *Circulation*. June 1981; 63(6):1259-1272). Similarly, MR perfusion imaging can quantify MBF in absolute terms, but requires the accurate characterization of the AIF. Christian and colleagues extended a method suggested by Jerosch-Herold et al that used a dual-bolus approach to MR perfusion imaging (Jerosch-Herold M, Wilke N, Stillman AE. Magnetic resonance quantification of the myocardial perfusion reserve with a Fermi function model for constrained deconvolution. *Med Phys*. January 1998; 25(1):73-84). Using this method, designed to more accurately quantify the arterial input function from MR perfusion images, they demonstrated accurate MR-derived MBF measurements from 0 to >5 ml/g/min compared with microsphere measurements (R=0.95) (Christian T F, Rettmann D W, Aletras A H, et al. Absolute myocardial perfusion in canines measured by using dual-bolus first-pass MR imaging. *Radiology*. September 2004; 232(3):677-684).

Our study demonstrates that the AIF can be extracted from the combination of bolus tracking and a single time-registered helical MDCT scan using protocols designed for non-invasive coronary angiography. In dynamic bolus tracking mode, MDCT scanners can image contrast kinetics in the aorta or LV blood pool in real-time and thus provide time-attenuation curves for the initial portion of the AIF. When bolus tracking detects an AD threshold suitable for coronary angiography and helical MDCT imaging begins, each image in the axial plane can be assigned a mean time of image acquisition when accounting for helical pitch, gantry rotation time, slice position, and slice thickness. Accordingly, arterial and LV blood pool attenuation densities can be used to complete the time-attenuation curve for the latter portion of the AIF that is delivered to the myocardium before and during helical MDCT imaging.

The attenuation of X-rays by iodinated contrast is directly proportional to the iodine concentration in tissue. Like Gd-DTPA used in MRI, iodinated contrast agents are diffusible tracers and the concentration of iodine measured in the myocardium is from a combination of perfusion and diffusion, with both being influenced by MBF (Canty J M, Jr., Judd R M, Brody A S, et al. First-pass entry of nonionic contrast agent into the myocardial extravascular space. Effects on radiographic estimates of transit time and blood volume. *Circulation*. November 1991; 84(5):2071-2078; Tong C Y, Prato F S, Wisenberg G, et al. Measurement of the extraction efficiency and distribution volume for Gd-DTPA in normal and diseased canine myocardium. *Magn Reson Med*. September 1993; 30(3):337-346; Tweedle MF. Physicochemical properties of gadoteridol and other magnetic resonance contrast agents. *Invest Radiol*. August 1992; 27 Suppl 1:S2-6). Thus, early, during the first-pass of iodinated contrast through the myocardium, differences in myocardial perfusion are represented by differences in myocardial attenuation and these difference may be used as a surrogate index of myocardial perfusion (George R T, Silva C, Cordeiro M A, et al. Multidetector computed tomography myocardial perfusion imaging during adenosine stress. *J Am Coll Cardiol*. Jul. 4 2006; 48(1):153-160).

Clinical Implications

MDCT, compared with MR and radionuclide MPI, can have several unique advantages including short scanning times and unsurpassed spatial resolution. By combining non-invasive angiography and perfusion imaging into a single exam, MDCT could simultaneously image atherosclerosis and its functional consequence to the myocardium. Furthermore, indeterminate MDCT angiograms with severe calcifications or motion artifacts could benefit from a measurement of myocardial perfusion and detect the presence or absence of a physiologically significant stenosis. This added information can be acquired without the time and expense a second imaging modality would entail. Moreover, this technique avoids the additional radiation patients undergo when radionuclide MPI is added to MDCT angiography.

The current study demonstrates that myocardial perfusion can be assessed during adenosine stress, first-pass MDCT imaging using a novel analysis method. While this method falls short of the absolute quantification of MBF, it provides an accurate semi-quantitative assessment of myocardial perfusion.

This study in this example was limited to stress imaging only. While it is preferable to perform rest and stress imaging, rest and stress imaging would require higher doses of nephrotoxic contrast and radiation. Furthermore, the ascertainment of rest flows in the open chest model utilized in this study is difficult to achieve. With the goal of translating the results of this preclinical study into patients, we chose to perform stress imaging only.

MDCT imaging systems require a pause in imaging between dynamic bolus tracking and helical MDCT imaging. This pause is needed so that the tube current can be increased and the collimators can moved. Therefore, interpolation of time-attenuation data is required between dynamic bolus tracking and helical imaging. In the current study, we limited this delay to 3.6 seconds. It should be possible to make this delay even shorter.

This example uses the myocardial AD acquired during helical MDCT imaging. This method, however, is limited since it does not allow the full elucidation of contrast kinetics in the myocardium. The ratio of the myocardial AD and the AUC of the AIF likely, more closely, reflect myocardial blood volume and studies have demonstrated that myocardial blood volume measurements can show regions of reduced perfusion relative to non-compromised myocardium. And, this study demonstrates, the myocardial AD, when normalized to the area under the time-attenuation curve constructed from time-registered helical MDCT imaging data with or without bolus tracking image data provides robust semi-quantitative metrics that correlate well with microsphere myocardial blood flow measurements.

Adenosine-mediated tachycardia can significantly degrade the quality of MDCT imaging. To offset this effect, adequate hydration and beta blockers were used to blunt the tachycardia response.

Lastly, beam-hardening artifacts can lower measured attenuation densities in the myocardium and LV blood pool, and thus impair the ability to quantify myocardial perfusion. Obvious beam hardening artifacts were easily identified in this study by their unique characteristics that include a triangular, transmural, and hypoenhanced appearance emanating from a structure with a high AD and they did not follow the distribution of a coronary vascular bed.

CONCLUSIONS

The combination of bolus tracking and time-registered helical imaging provides a novel method to reconstruct the AIF using protocols designed for non-invasive coronary angiography. The accurate assessment of the AIF is an essential part of quantitative perfusion imaging and measured MDCT myocardial attenuation densities, when normalized to the AIF, provide more accurate semi-quantitative metrics of myocardial perfusion that compare well to microsphere derived MBF. The ability to assess myocardial perfusion during an MDCT non-invasive coronary angiogram could have significant implications in the diagnosis, prognosis, and treatment of coronary artery disease.

TABLE 1

Myocardial perfusion measurements using four different metrics of MDCT myocardial perfusion in stenosed versus remote territories.

| | Stenosed Territory | Remote Territory | $R^2$ | p-Value |
|---|---|---|---|---|
| Mean Myocardial AD | 104 ± 32 | 161.4 ± 40 | 0.75 | <0.001 |
| Mean $MYO_{AD}$/Mean $LV_{AD}$ Ratio | 0.20 ± 0.07 | 0.31 ± 0.11 | 0.79 | <0.001 |
| Mean $MYO_{AD}$/Entire AUC Ratio | 0.015 ± 0.004 | 0.023 ± 0.006 | 0.82 | <0.001 |
| Mean $MYO_{AD}$/Helical AUC Ratio | 0.019 ± 0.006 | 0.030 ± 0.009 | 0.86 | 0.001 |

Values are mean ± standard deviation.

The current invention is not limited to the specific embodiments of the invention illustrated herein by way of example, but is defined by the claims. One of ordinary skill in the art would recognize that various modifications and alternatives to the examples discussed herein are possible without departing from the scope and general concepts of this invention.

We claim:

1. A computed tomography system, comprising:
a support stage constructed and arranged to support a subject while under observation;
an x-ray illumination system arranged proximate said support stage to illuminate said subject with x-rays;
an x-ray detection system arranged proximate said support stage to detect x-rays after they pass through said subject and to provide signals based on the detected x-rays; and
a data processing system in communication with said x-ray detection system to receive said signals from said x-ray detection system,
wherein said computed tomography system has a dynamic mode of operation in which said x-ray illumination system illuminates a portion of said subject a plurality of times and said data processing system processes at least some of said signals from said x-ray detection system to obtain a plurality of dynamic mode computed tomography images of said portion of said subject corresponding to said plurality of times to provide information regarding a change in said portion of said subject over said plurality of times,
wherein said computed tomography system has a scanning mode of operation in which said x-ray illumination system illuminates a plurality of portions of said subject and said data processing system processes at least some of said signals from said x-ray detection system to obtain a plurality of scanning mode computed tomography images of a corresponding plurality of portions of said subject to provide a substantially three-dimensional representation of an internal structure of said subject,
wherein said data processing system is configured to time register said plurality of dynamic mode computed tomography images with said plurality of scanning mode computed tomography images,
wherein said data processing system is further configured to determine a first portion of an arterial input function based on said plurality of dynamic mode computed tomography images after being time registered, and
wherein said data processing system is further configured to determine a second portion of said arterial input function based on said plurality of scanning mode computed tomography images after being time registered.

2. A computed tomography system according to claim 1, wherein said dynamic mode of operation provides bolus tracking of a contrast agent at least one of injected or being injected into said subject such that said change in said portion of said subject over said plurality of times corresponds to changes in images of said contrast agent.

3. A computed tomography system according to claim 2, wherein said bolus tracking provides at least one of myocardial blood flow or myocardial perfusion information.

4. A computed tomography system according to claim 2, wherein said scanning mode is a helical scanning mode in which said x-ray illumination system and said x-ray detection system take a helical path around at least a portion of said subject.

5. A computed tomography system according to claim 1, wherein said scanning mode is a helical scanning mode in which said x-ray illumination system and said x-ray detection system take a helical path around at least a portion of said subject.

6. A computed tomography system according to claim 1, wherein said x-ray detection system comprises an array of x-ray detectors such that said computed tomography system is a multidetector computed tomography system.

7. A computed tomography system according to claim 1, wherein said information concerning said dynamic process of said subject provides at least an approximation of an arterial input function for said subject under observation.

8. A computed tomography system according to claim 1, wherein said information concerning said dynamic process of said subject provides information concerning myocardial perfusion for said subject under observation.

9. A computed tomography system according to claim 1, wherein said data processing system extracts said information concerning said dynamic process of said subject such that times corresponding to each of the plurality of computed tomography images during said dynamic mode are related to times of each of said plurality of computed tomography images of said corresponding plurality of portions of said subject.

10. A computed tomography system according to claim 1, wherein said computed tomography system has a pause time in which said x-ray illumination system is turned off for changing between said dynamic mode of operation and said scanning mode of operation.

11. A computed tomography system according to claim 10, wherein said data processing system extracts said information concerning said dynamic process of said subject such that times corresponding to each of the plurality of computed tomography images during said dynamic mode are related to times of each of said plurality of computed tomography images of said corresponding plurality of portions of said subject including taking into account said pause time.

12. A computed tomography system according to claim 10, wherein said pause time is less than about 5 seconds.

13. A computed tomography system according to claim 10, wherein said pause time is less than about 3.5 seconds.

14. A computed tomography system according to claim 10, wherein said pause time is substantially zero.

15. A computed tomography system according to claim 11, wherein said scanning mode is a helical scanning mode in which said x-ray illumination system and said x-ray detection system take a helical path around at least a portion of said subject.

16. A computed tomography system according to claim 15, wherein said times of each of said plurality of computed tomography images of said corresponding plurality of portions of said subject from said helical scanning mode are determined based on information concerning a corresponding image slice position, an image slice thickness, a helical pitch of said helical mode and a gantry rotation time of the x-ray illumination and x-ray detection systems during a helical scan.

17. A computed tomography system according to claim 16, wherein said times of each of said plurality of computed tomography images are determined based on the formula $$\text{Time(Secs)} = \frac{\Delta D \cdot GRT}{ST \cdot HP},$$

where Time is the mean time in seconds of image acquisition, $\Delta D$ is the change in distance in a longitudinal axis with respect to a most cranial acquired axial slice, GRT is the gantry rotation speed, ST is the image slice thickness, and HP is the helical pitch.

18. A computed tomography system according to claim 1, wherein said scanning mode is a non-helical scanning, and wherein said times of each said plurality of computed tomography images are determined based on actual times of longitudinal image acquisition.

19. A computed tomography system according to claim 1, wherein said support stage is a movable support stage configured to move said subject in an axial direction during said scanning mode of operation.

20. A computed tomography system according to claim 19, wherein each of said plurality of computed tomography images corresponds to a different, discrete displacement of said support stage along said axial direction.

21. A method of processing x-ray signals, comprising:
receiving signals detected from x-rays that have passed through a subject under observation during a dynamic mode of operation in which an x-ray illumination system illuminates a portion of said subject a plurality of times;
processing said signals received from said dynamic mode of operation to obtain a plurality of dynamic mode computed tomography images of said portion of said subject corresponding to said plurality of times to provide information regarding a change in said portion of said subject over said plurality of times;
receiving signals detected from x-rays that have passed through said subject under observation during a scanning mode of operation in which said x-ray illumination system illuminates a plurality of portions of said subject;
processing said signals received during said scanning mode of operation to obtain a plurality of scanning mode computed tomography images of a corresponding plurality of portions of said subject to provide a substantially three-dimensional representation of an internal structure of said subject;
time-registering said plurality of dynamic mode computed tomography images with said plurality of scanning mode computed tomography images;
determining a first portion of an arterial input function based on said plurality of dynamic mode computed tomography images after said time-registering; and
determining a second portion of said arterial input function based on said plurality of scanning mode computed tomography images after said time-registering.

* * * * *